United States Patent [19]

Cook et al.

[11] 4,216,227

[45] Aug. 5, 1980

[54] OMEGA-AMINO ACID ESTER HYDROCHLORIDES FOR TREATING BACTERIAL INFECTIONS

[76] Inventors: Elton S. Cook, 1842 Madison Rd., Cincinnati, Ohio 45206; Akira Fujii, 870-1 Sakaecho, Nishi-2, Matsudo-shi, Chiba-ken, Japan

[21] Appl. No.: 927,059

[22] Filed: Jul. 24, 1978

[51] Int. Cl.$^2$ ..................... A61K 31/22; A61K 31/23
[52] U.S. Cl. ..................................... 424/311; 424/312
[58] Field of Search ............................... 424/311, 312

[56] References Cited

PUBLICATIONS

Chemical Abstracts 62:16566f (1965).

Primary Examiner—Jerome D. Goldberg
Attorney, Agent, or Firm—Kinney & Schenk

[57] ABSTRACT

Although many antimicrobials have been suggested for the treatment of coccic and bacillic infections, such diseases continue to be a problem. These bacteria are unique in the subtleties of their infections due to the unpredictable vagaries of the organisms. The frequent appearance of new antibiotic resistant strains of coccus and bacillus, and the reappearance of the same strain, even after apparent successful eradication, suggest the need for additional antimicrobials for combatting the infections. Such new antimicrobials are provided herein.

6 Claims, No Drawings

OMEGA-AMINO ACID ESTER HYDROCHLORIDES FOR TREATING BACTERIAL INFECTIONS

BACKGROUND OF THE INVENTION

This invention pertains to antimicrobials effective in protecting against cocci and bacilli bacterial infections.

Although many antimicrobials have been suggested for the treatment of coccic and baccilic infections, such diseases continue to be a problem. The reason for this is that bacteria embodying within themselves an array of yet unanswered puzzles in biology, both fundamental and experimental. They are ubiquitous in distribution and have attained extreme degrees of diversification in biological and biochemical characteristics. It is recognized that the significance of staphylococcal infections is not so much in severity, except in a few instances, as in the subtleties of the infection due to the unpredictable vagaries of these organisms.

Treatment, of diseases caused by cocci and bacilli is complicated by the ability of the organisms to develop resistance. The magnitude of the problem is further amplified by the extreme difficulty of total eradication, and the frequent reappearance of the same strain even after apparent successful elimination. The inability to eliminate the carrier state by any of the currently known methods and the prevalence of the new antibiotic resistant hospital strains have added a new dimension to the frustrating situation. The development of such multiple antibiotic resistant strains of the organism suggests the desirability of investigating additional means of combatting the infections. As a consequence the development of antimicrobials which are effective against coccic and bacillic infections has attracted considerable attention.

As shown by such prior art U.S. Pat. Nos. as 3,629,451, 3,728,444, and 3,843,798 we have previously found certain natural amino acids, those found in organ extracts, such as brain, spleen, kidney, and heart, to be antistaphylococcal and antistreptococcal agents. Accordingly it was decided to investigate the anticoccic activity of long carbon chain alcohols. However, such alcohols have been found to be toxic ($LD_{50}$, approximately 4.5–5.0 gm/kg for rat—oral). This invention overcomes this toxicity problem.

SUMMARY OF THE INVENTION

In accordance with the practice of this invention a new antimicrobial is provided conferring on mammals remarkable resistance to coccus and bacillus infections. The approach is to administer to a mammal suffering from said bacterial infection an antibacterial effective amount of a hydrochloride of an omega-amino acid ester of a $C_6$-$C_{10}$ saturated aliphatic alcohol. The invention thus provides an antimicrobial effective in inducing resistance to bacterial infections, yet without itself being alive.

DETAILED DESCRIPTION OF THE INVENTION

Our investigation of aliphatic alcohols showed that the in vitro antistaphylococcal activity of $C_6$ through $C_{10}$ saturated aliphatic alcohols is quite high. However their in vivo antistaphylococcal activity in mice was found to be ten or less expressed as $ASA = (M_c - M_e)/M_c J/C$ wherein $M_c$ is the mortality of the untreated negative control, $M_e$ is the mortality of the treated (experimental) animals, and C is the dose in millimols. Quite unexpectedly, we found that when the alcohol was esterified with an $\omega$-amino acid the antistaphylococcal activity in vivo was significantly increased.

This illustrated that the processes of infection leading to coccic infections are problems in the ecology of the parasite. It is also being increasingly realized that the bacterial and host determinants are closely interrelated. Staphylococcal virulence derives from the combined action of several bacterial factors whose effectiveness is conditioned by the reactions of the host. Perhaps the most striking feature of host-parasite relationships in staphylococcal infections is the relatively atypical immunologic response. Human studies have given convincing evidence that most adult humans possess an array of antistaphylococcal antibodies. Nevertheless resistance to staphylococcal infections seems to be governed to a considerable extent by other unrelated factors. Thus the antistaphylococcal activity in vivo found herein appears to be due, not only to antimicrobial action, but to the fact that in the system of the host the antimicrobials create an environment in which the organism does not grow. They render immunity to the host, as does a vaccine, but without the organism itself being present as it is in vaccines.

The compositions of this invention thus constitute a significant new class of antimicrobials. Specifically they are esters of omega-amino acids having the formula $H_2N(CH_2)_n COO(CH_2)_{n'} CH_3 \cdot HCl$ where n and n' are natural numbers, n being 1 through 7, and n' being 5 through 9. It is contemplated that they will be taken orally, or by intramuscular injection.

The antimicrobials which are preferred herein are hydrochlorides of hexyl, octyl, and decyl, alcohol esters of omega-amino acetic, propionic, butyric, valeric, hexanoic, heptanoic, and octanoic acids. These omega-amino acid ester hydrochlorides were prepared by the esterification of the omega-amino acid with an excess of the alcohol with dry HCl gas. The mixture of amino acid and alcohol was heated to about 150° C. for three hours with continuous stirring and feeding of dry HCl gas. The mixture was then concentrated in vacuo, treated with ligroin, and cooled to give crystals of the hydrochlorides of the esters.

The high degree of resistance to staphylococcal infections obtained by omega-amino acid ester hydrochlorides will best be apparent from their biological effects in in vitro and in vivo tests. The antistaphylococcal activity in vitro was determined using the paper disk method. The concentration of the compounds was 0.2 mg/disk. The activity is expressed as the growth inhibitory area. In the in vivo tests antistaphylococcal activity was determined using BDF mice, both male and female. The animals were between 10 and 14 weeks old, males having approximate average weights of 12 to 19 grams, females having approximate average weights of 18 to 24 grams. For the most part the mice were raised and maintained on the Rockland diet.

The assays were conducted using a penicillin-resistant strain, *Staphylococcus aureus* Original, first isolated from a case of acute tonsilitis and maintained in our laboratories for years. This strain is preserved in the lyophilized form and stored at 0° C., and stock cultures were raised on SA 110 slants once in every 6 months. For testing, the inoculum was prepared as 24 hour cultures from Bacto-staphylococcus Medium 110. The cells were washed and suspended in physiological saline (TC Tyrode Solution, Difco). In contrast to conventional procedures, a dose killing 80 to 90 percent ($LD_{80-90}$) instead of a dose killing 50 percent ($LD_{50}$) was used in these investigations. This has been the practice in our laboratories in studies with staphylococci since lower dosages often fail to give adequate degrees of mortality. The $LD_{80-90}$ was determined by injecting groups of mice subcutaneously with different dilutions of the bacterial suspension and noting the mortality over a 5-day period.

Using groups of twenty-two to twenty-four mice, the animals were inoculated subcutaneously with the compounds to be tested two hours before and four hours after challenge with a 60 percent suspension of the "Original Strain" organism. Antistaphylococcal activity was determined using 5 mg doses per mouse of the omega-amino acid ester hydrochloride in cottonseed oil. Antistaphylococcal activity in vivo is expressed as effectiveness of protection using ASA values as defined hereinbefore. Results of the tests are given in the following table.

ANTISTAPHYLOCOCCAL ACTIVITIES IN VIVO AND IN VITRO, AND $R_m$ VALUES OF ESTERS OF ω-AMINO ACIDS

| COMPD | n | n' | ANTISTAPHYLOCOCCAL ACTIVITY IN VIVO, ASA mm² | IN VITRO, AREA OF INHIBITION |
|---|---|---|---|---|
| 2Aac-OHe | 1 | 5 | 19.3 | 0.0 |
| 3Apr-OHe | 2 | 5 | 31.3 | 0.0 |
| 4Abu-OHe | 3 | 5 | 23.9 | 0.0 |
| 5Avl-OHe | 4 | 5 | 35.7 | 0.0 |
| 6Ahx-OHe | 5 | 5 | 50.0 | 1.0 |
| 7Ahp-OHe | 6 | 5 | 52.6 | 15.9 |
| 8Aoc-OHe | 7 | 5 | 43.7 | 28.8 |
| 2Aac-OOc | 1 | 7 | 36.4 | 12.6 |
| 3Apr-OOc | 2 | 7 | 28.6 | 17.7 |
| 4Abu-OOc | 3 | 7 | 30.0 | 15.7 |
| 5Avl-OOc | 4 | 7 | 33.9 | 17.3 |
| 6Ahx-OOc | 5 | 7 | 55.6 | 20.0 |
| 7Ahp-OOc | 6 | 7 | 27.5 | 20.0 |
| 8Aoc-OOc | 7 | 7 | 0.0 | 19.7 |
| 2Aac-ODe | 1 | 9 | 50.0 | 44.9 |
| 3Apr-ODe | 2 | 9 | 21.1 | 33.3 |
| 4Abu-ODe | 3 | 9 | 22.2 | 12.9 |
| 5Avl-ODe | 4 | 9 | 23.5 | 14.0 |
| 6Ahx-ODe | 5 | 9 | 25.0 | 7.8 |
| 7Ahp-ODe | 6 | 9 | 25.0 | 9.8 |
| 8Aoc-ODe | 7 | 9 | 13.3 | 0.0 |
| L-Ala | | | — | — |
| HeOH | | | 10.2 | 44.7 |
| OcOH | | | 9.3 | 69.2 |
| DeOH | | | 5.3 | 128.8 |

In the table are data showing the anticoccic activity in vivo, ASA, and in vitro, of the esters and their component alcohols. The ASA values of component ω-amino acids and alcohols are all 10 or less, except 5-amino valeric acid which is 13.1. Hence, by forming the esters of ω-amino acids we have markedly increased the antistaphylococcal activity. The antistaphylococcic activity in vitro of ω-amino acids are all 0 and alcohols are much higher than the ester hydrochlorides. This indicates that by forming the ester hydrochlorides of the ω-amino acids, the in vitro antibiotic action of alcohols was lowered significantly. However, as indicated hereinbefore, the antistaphylococci activity in vivo was clearly increased. Hence by forming the ester hydrochlorides of ω-amino acids it is possible to form compounds which have lower antimicrobial action in vitro, indicating lower toxicity, but which have higher antimicrobial action in vivo. The data also shows that among these compounds octyl-6-amino hexanoate gave the greatest in vivo antistaphylococcal activity.

It is evident that the compositions of this invention constitute an important new class of antistaphylococcal agents. The omega-amino acid ester hydrochlorides of long chain saturated alcohols were found to possess antistaphylococcic activity which was superior to that of the component acids and alcohols. All of the compounds were homogenous with five different solvents. They can, therefore, be combined with such solvents for injection, sodium chloride being used if necessary to render the solution isotonic. It is also noted that the toxicity of the long chain saturated alcohols is decreased by forming esters of the omega-amino acids.

The ester hydrochlorides of the invention can also be taken orally, in, say, 250 to 500 milligram tablets. Where exposure to coccic infections is likely, such as on entering a hospital, these tablets, or 150 to 500 mg injections will be prescribed. Solutions or suspensions for injection will contain 0.1 to 5 percent, preferably 0.1 to 1.5 percent of the antimicrobial by weight. In the case of tablets, if desired, suitable colorants, adhesives, and lubricants will be incorporated, along with a solid pharmaceutical diluent, for instance starch, lactose, sucrose, and other pharmaceutical diluents. These tablets will contain 50 percent of a long chain alcohol ester hydrochloride of an omega-amino acid on a weight basis. Capsules can also be made. Consequently a process is provided for the control of infections in humans and other mammals due to cocci which involves administering to the mammal an effective amount of the ester hydrochlorides of the invention. Various mixtures, doses, and other variations and modifications of the antimicrobials will occur to those skilled in the art. For instance, it will be appreciated that tablets will be administered more frequently than injections. Such ramifications are deemed to be within the scope of this invention.

What is claimed is:

1. A method of treating a bacterial infection in a mammal comprising administering to said mammal suffering from said bacterial infection an antibacterial effective amount of an omega-amino acid ester having the formula $H_2N(CH_2)_nCOO(CH_2)_{n'}CH_3 \cdot HCl$ wherein n is a natural number 1 through 7 and n' is a natural number 5 through 9.

2. The method of claim 1 wherein n is 5 and n' is 7.
3. The method of claim 1 wherein n is 5 and n' is 5.
4. The method of claim 1 wherein n is 1 and n' is 9.
5. The method of claim 1 wherein n is 7 and n' is 5.
6. The method of claim 1 wherein n is 1 and n' is 7.

* * * * *